US009788863B2

(12) United States Patent
Juchno et al.

(10) Patent No.: US 9,788,863 B2
(45) Date of Patent: Oct. 17, 2017

(54) POSTERIOR LUMBAR PLATE

(71) Applicant: GLOBUS MEDICAL, INC., Audubon, PA (US)

(72) Inventors: Brad Juchno, Yardley, PA (US); Kurt Faulhaber, Plymouth Meeting, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 220 days.

(21) Appl. No.: 13/657,310

(22) Filed: Oct. 22, 2012

(65) Prior Publication Data

US 2014/0114314 A1    Apr. 24, 2014

(51) Int. Cl.
*A61B 17/70*    (2006.01)
*A61B 17/80*    (2006.01)
*A61B 17/86*    (2006.01)

(52) U.S. Cl.
CPC ...... *A61B 17/7007* (2013.01); *A61B 17/7032* (2013.01); *A61B 17/7037* (2013.01); *A61B 17/8047* (2013.01); *A61B 17/8685* (2013.01)

(58) Field of Classification Search
CPC ............ A61B 17/8047; A61B 17/8057; A61B 17/8052; A61B 17/7007
USPC ............................................ 606/70, 71, 252
See application file for complete search history.

(56) References Cited

U.S. PATENT DOCUMENTS

| 4,836,196 | A |  | 6/1989 | Park |  |
|---|---|---|---|---|---|
| 4,913,134 | A |  | 4/1990 | Luque |  |
| 5,261,910 | A |  | 11/1993 | Warden |  |
| 5,269,784 | A | * | 12/1993 | Mast | A61B 17/60 606/286 |
| 5,578,034 | A | * | 11/1996 | Estes | A61B 17/8047 411/909 |
| 5,735,853 | A | * | 4/1998 | Olerud | A61B 17/7059 606/289 |
| 5,800,435 | A |  | 9/1998 | Errico |  |
| 6,017,345 | A |  | 1/2000 | Richelsoph |  |
| 6,287,309 | B1 |  | 9/2001 | Baccelli |  |
| 6,315,779 | B1 |  | 11/2001 | Morrison |  |
| 6,641,583 | B2 |  | 11/2003 | Shluzas |  |
| 6,689,133 | B2 |  | 2/2004 | Morrison |  |
| 7,220,263 | B2 |  | 5/2007 | Cordaro |  |
| 7,252,670 | B2 |  | 8/2007 | Morrison |  |
| 7,771,458 | B2 |  | 8/2010 | Biedermann |  |
| 7,789,899 | B2 |  | 9/2010 | Markworth |  |
| 7,883,531 | B2 |  | 2/2011 | de Coninck |  |
| 7,938,848 | B2 |  | 5/2011 | Sweeney |  |
| 2002/0143328 | A1 | * | 10/2002 | Shluzas et al. | 606/61 |
| 2003/0078583 | A1 | * | 4/2003 | Biedermann | A61B 17/7059 606/290 |
| 2003/0093077 | A1 |  | 5/2003 | Schlapfer et al. |  |

(Continued)

*Primary Examiner* — David Bates
*Assistant Examiner* — Olivia C Chang

(57) ABSTRACT

The present invention relates to stable fixation of spine segments, allowing for fusion in, e.g., skeletally mature patients. More particularly, the invention relates to a bone fixation device that can be affixed to vertebrae of a spine to provide reduction (or enlargement) capabilities and allow for fixation in the treatment of various conditions, including, e.g., spondyloslisthesis, degenerative disc disease, fracture, dislocation, spinal tumor, failed previous fusion, and the like, in the spine. The invention also relates to a method for delivering and implanting the bone fixation device.

11 Claims, 8 Drawing Sheets

(56) References Cited

U.S. PATENT DOCUMENTS

| | | |
|---|---|---|
| 2004/0177847 A1 | 9/2004 | Foley et al. |
| 2005/0154392 A1* | 7/2005 | Medoff ............. A61B 17/8047 606/287 |
| 2005/0216001 A1* | 9/2005 | David ................ A61B 17/7007 606/281 |
| 2006/0184170 A1 | 8/2006 | Kapitan et al. |
| 2007/0010817 A1 | 1/2007 | de Coninck |
| 2007/0118126 A1* | 5/2007 | Medoff et al. .................. 606/69 |
| 2007/0270820 A1 | 11/2007 | Dickinson et al. |
| 2009/0281571 A1 | 11/2009 | Weaver et al. |
| 2010/0222779 A1 | 9/2010 | Ziemek et al. |
| 2010/0274294 A1 | 10/2010 | Biedermann et al. |
| 2012/0158056 A1 | 6/2012 | Blain |
| 2013/0165980 A1* | 6/2013 | Cook ................ A61B 17/8047 606/286 |

* cited by examiner

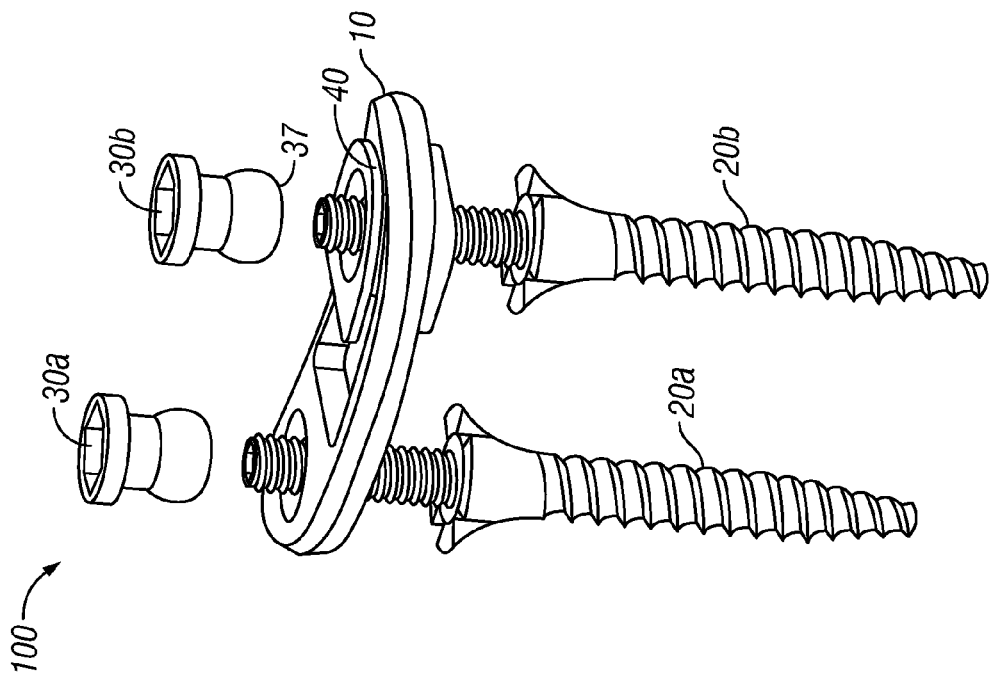
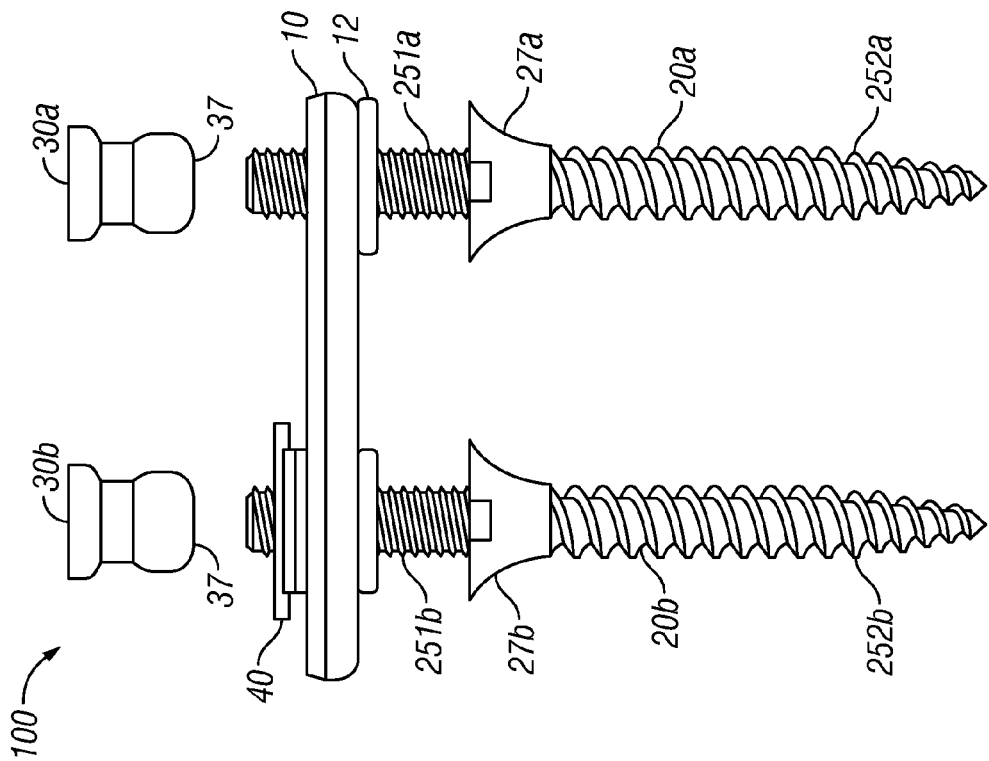

POSTERIOR LUMBAR PLATE

FIELD OF THE INVENTION

The present invention relates to stable fixation of spine segments, allowing for fusion in, e.g., skeletally mature patients. More particularly, the invention relates to a bone fixation device that can be affixed to vertebrae of a spine to provide reduction (or enlargement) capabilities and allow for fixation in the treatment of various conditions, including, e.g., spondyloslisthesis, degenerative disc disease, fracture, dislocation, spinal tumor, failed previous fusion, and the like, in the spine. The invention also relates to a method for delivering and implanting the bone fixation plating device.

BACKGROUND OF THE INVENTION

Bones and bony structures are susceptible to a variety of weaknesses that can affect their ability to provide support and structure. Weaknesses in bony structures can have many causes, including degenerative diseases (e.g., degenerative disc diseases), tumors, fractures, dislocations and failed previous fusions. Some of these weaknesses can cause further conditions such as spondylolisthesis wherein bony structures slip out of their proper position.

In some cases of spinal surgery, it is known to use bone fixation plating devices (e.g., bone plate systems and rod and screw systems) to improve the mechanical stability of the spinal column and to promote the proper healing of injured, damaged or diseased spinal structures. Typically, corrective surgery can entail the removal of damaged or diseased tissue, a decompression of one or more neural elements, followed by the insertion of an interbody implant or bone graft for the purposes of a fusion or disc arthroplasty. In cases where spinal fusion is the desired surgical outcome, the surgery can often include implanting a bone plate or rod and screw system in order to immobilize adjacent vertebral bones to expedite osteogenesis across the vertebral segments. Accordingly, there is a need to improve on bone fixation plating devices.

SUMMARY OF THE INVENTION

The present invention includes a bone fixation plating device and a method for delivering and implanting the bone fixation plating device in a patient. The bone fixation plating device can be affixed to vertebrae of a spine of the patient to facilitate bony fusion and stabilization of the spine. The method includes delivering the bony fixation device to a treatment area of the spine, and affixing the device to vertebrae of the spine to, e.g., facilitate bony fusion and stabilization of the spine.

In some embodiments, a bone fixation plating device is provided for therapeutic treatment of a patient, the device comprising: a plate having a locking device receiving hole and a carriage receiving slot, wherein the locking device receiving hole and the carriage receiving slot are adjacent to one another and the locking device receiving hole is configured to receive and pass there-through a portion of a first screw; and a carriage comprising an intermediate portion that is configured to fit in the carriage receiving slot, the carriage comprising a hole to receive and pass there-through a portion of a second screw.

In some embodiments, the carriage can comprise an upper flange and a lower flange. The carriage can comprise a two piece assembly that includes an upper carriage portion and a lower carriage portion. In some embodiments, the carriage can be a single piece structure. One of the upper flange and the lower flange can comprise an indentation that is configured to engage a guide in the carriage receiving slot. One of the upper flange and the lower flange can comprise a reverse bevel.

The device can further comprise a further carriage that is configured to fit in the carriage receiving slot together with said carriage, said further carriage comprising a hole to receive and pass there-through a portion of a screw, wherein said carriage and said further carriage are movable in the carriage receiving slot along a longitudinal axis of the plate.

The device can further comprise a screw having a post. The screw can comprise a first thread and a second thread, wherein one of the first and second threads comprises a fine thread. The other of the first and second threads can comprise a coarse thread. A proximal end of the screw can comprise an open-ended guide wire capture slot. The threaded shaft of each of the two bone screws can be tapered at the distal end.

The device can further comprise a locking device. The locking device can comprise a cutout. The locking device receiving hole of the plate can comprise a rib that is configured to lockably engage the locking device. The locking device can comprises a ball shape or a tulip shape.

According to a further aspect of the invention, a bone fixation plating device is provided for therapeutic treatment of a patient, the device comprising: a plate having a locking device receiving hole and a carriage receiving slot, wherein the locking device receiving hole and the carriage receiving slot are adjacent to one another and the locking device receiving hole is configured to receive and pass there-through a portion of a first screw; a carriage comprising an intermediate portion that is configured to fit in the carriage receiving slot, the carriage comprising a hole to receive and pass there-through a portion of a second screw; and a locking device that is configured to fasten to one of said first and second screws and secure the plate to the first and second screws. The carriage can comprise a two piece assembly that includes an upper carriage portion and a lower carriage portion, or a single piece structure, wherein the carriage is movable in the carriage receiving slot along a longitudinal axis of the plate. One of the upper flange and the lower flange can comprise an indentation that is configured to engage a guide in the carriage receiving slot.

According to a further aspect of the invention, a method is provided for implanting a bone fixation plating device, the method comprising: positioning a plate having a locking device receiving hole and a carriage receiving slot that includes a carriage proximate to a plurality of screws that have been implanted in bony structures; mounting the plate and carriage on to respective portions of the plurality of screws; securing the plate and carriage to the plurality of screws with an equal number of locking devices. The method can further comprise adjusting the location of the carriage with respect to the locking device receiving hole based on the spacing between the plurality of screws. The method can further comprise selecting a plate length and curvature based on the spacing of the screws and the anatomical needs of the patient. The method can further comprise contouring, twisting, and/or bending the plate based on the anatomical needs of the patient.

Additional features, advantages, and embodiments of the invention can be set forth or apparent from consideration of the following attached detailed description and drawings. Moreover, it is to be understood that both the foregoing summary of the invention and the following attached detailed description are exemplary and intended to provide further explanation without limiting the scope of the invention as claimed.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIGS. 2A and 2B show different partially exploded views of the bone fixation plating device of FIGS. 1A and 1B;

Figure 1A:
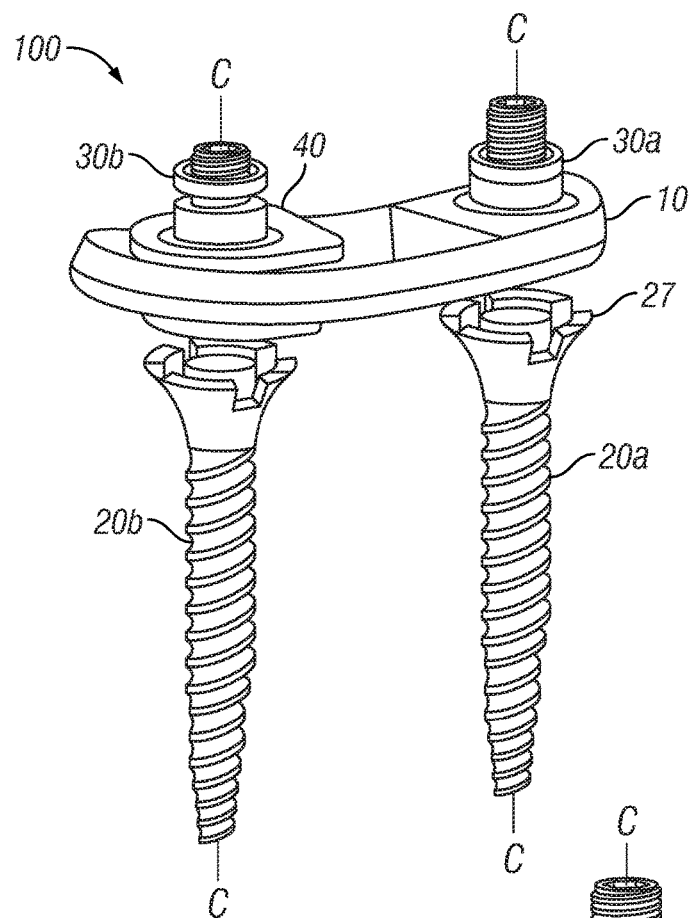
FIGS. 1A and 1B show different views of a bone fixation plating device that is constructed according to an embodiment of the invention.

The present invention is further described in the detailed description that follows.

DETAILED DESCRIPTION OF THE INVENTION

The aspects of the present invention and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect can be employed with other aspects as the skilled artisan would recognize, even if not explicitly stated herein. Descriptions of well-known components and processing techniques can be omitted so as to not unnecessarily obscure the aspects of the present invention. The examples used herein are intended merely to facilitate an understanding of ways in which the present invention can be practiced and to further enable those of skill in the art to practice the aspects of the present invention. Accordingly, the examples and aspects herein should not be construed as limiting the scope of the present invention, which is defined solely by the appended claims and applicable law. Moreover, it is noted that like reference numerals represent similar parts throughout the several views of the drawings.

The terms "a," "an," and "the," as used herein, are defined to mean "one or more," unless expressly specified otherwise. The terms "including," "having," "comprising," and variations thereof, as used herein, are defined to mean "including, but not limited to," unless expressly specified otherwise.

Figure 1B:
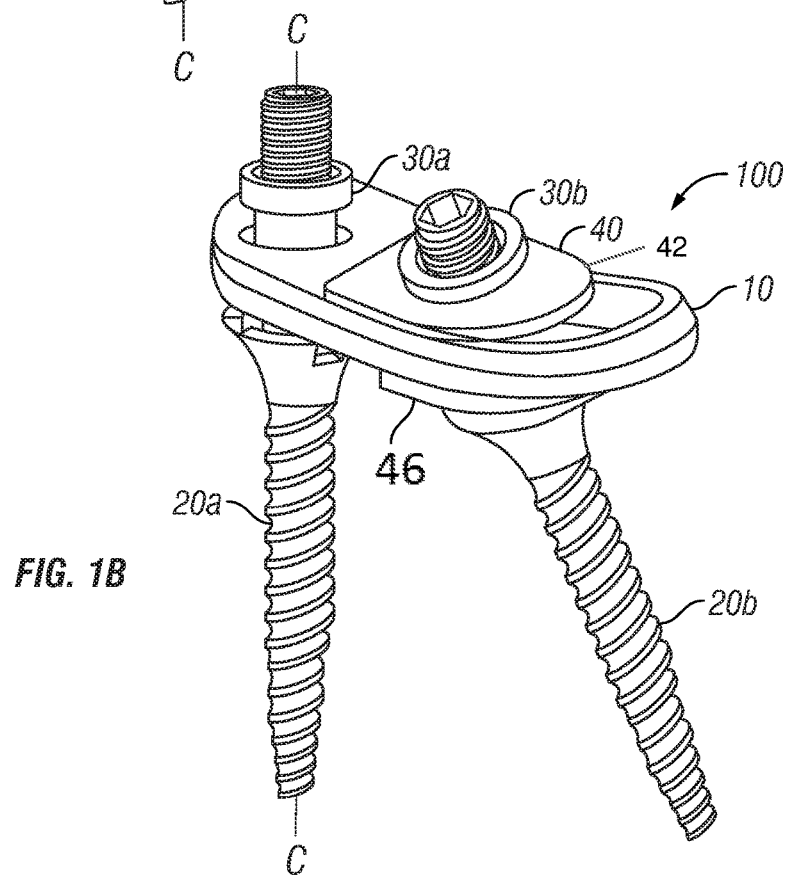

FIGS. 1A and 1B show different views of a bone fixation plating (or posterior lumbar implant) device 100 that is constructed according to an embodiment of the invention. The bone fixation plating device 100 comprises a bone fixation plate 10, a pair of posted bone screws 20 (identified individually as 20a and 20b), and a pair of locking balls 30 (identified individually as 30a and 30b). In some embodiments, bone screw 20b can be received in a carriage 40 that can slide along a length of the device 100 until a desired distance of separation between the posted screws 20a and 20b is achieved. Once a desired distance of separation has been achieved, the carriage 40 can be compressed and locked in place along the length of the plate 10. In addition, in some embodiments, the bone fixation plating device 100 is configured to allow the posted bone screws 20a and 20b to rotate and/or pivot polyaxially with regard to the bone fixation plate 10. Accordingly, the device 100 not only accommodates selective positioning of the screws 20a and 20b relative to one another, but also desirable polyaxial adjustment.

In FIG. 1A, the bone fixation plating device 100 is shown in an assembled (or substantially assembled) configuration, wherein the longitudinal axes C-C of the pair of posted bone screws 20a and 20b are aligned substantially parallel to each other and substantially perpendicular to a plane of the bone fixation plate 10.

In FIG. 1B, the bone fixation plating device 100 is shown in an assembled (or substantially assembled) configuration, wherein the longitudinal axes C-C of the pair of posted bone screws 20a and 20b are not parallel to each other, but instead, the longitudinal axis of one of the posted bone screws 20b is offset with respect to the longitudinal axis of the other posted bone screw 20a. Further, the longitudinal axis of one of the posted bone screws 20a is positioned substantially perpendicular to the plane of the bone fixation plate 10, and the longitudinal axis of the other posted bone screw 20b is positioned at an angle significantly less (or greater) than 90° (e.g., about 65°) with respect to the plane of the bone fixation plate 10. As seen in FIG. 1B, each of the posted bone screws 20 can advantageously be moved polyaxially in all directions at an angle of between, e.g., about 0° and about 80°, or between about 0° and about 25° with respect to an axis normal (or perpendicular) to the plane of the bone fixation plate 10. In some embodiments, the range of movement can be greater or less than about 0° to about 25°. Positioning of the bone screw 20a or 20b at an angle relative to an axis normal (or perpendicular) to the plane of the bone fixation plate 10 allows the plate 10 to accommodate for movements in the vertebrae and/or for compression of the bone grafts that are placed between vertebrae. In addition, by providing the bone screws 20a and 20b with polyaxial adjustability, this advantageously allows the plate to cooperate with a variety of different anatomies.

Further, as shown in FIGS. 1A and 1B, the device 100 allows for the relative positioning of the posted bone screws 20a and 20b to be modified. The device 100 provides a carriage 40 for at least one of the bone screws 20b, which allows the screw 20b to be adjusted along a length of the plate 10. In some embodiments, the other screw 20a, can be in a relatively fixed position along a length of the plate 10. As shown in FIG. 1B, the carriage 40 can include an upper flange 42 and a lower flange 46 that can ride along a length of the plate 10, such that the plate 10 serves as a track for the carriage 40. In some embodiments, as shown in FIG. 1B, the flanges 42 and 46 of the carriage 40 can extend along top and bottom surfaces of the plate 10. In alternative embodiments, the flanges 42 and 46 of the carriage 40 can extend within a recess formed in sidewalls of the plate 10. Once the bone screw 20b is placed in a desired position relative to the bone screw 20a, the carriage 40 can be compressed and secured onto the plate 10 (e.g., via downward application of the compression ball 30b along the top threads of the bone screw 20b, as discussed in more detail below), thereby preventing or restricting movement of the carriage 40 along the plate 10.

FIGS. 2A and 2B show different partially exploded views of the bone fixation plating device 100. In these views, the compression balls 30a and 30b have not yet been secured to the bone screws 20a and 20b. As shown in the figures, each of the bone screws 20a and 20b includes a top threaded section (251a, 251b) and a bottom threaded section (252a, 252b), The top threaded sections 251a, 251b of the screws pass through the plate 10 and accommodate the compression balls 30a, 30b, which are internally threaded, while the bottom threaded sections 252a, 252b are insertable into a vertebral body, such as the pedicle.

With respect to the first bone screw 20a, which is in a relatively fixed position along the length of the plate 10, the bone screw 20a can be polyaxially adjustable relative to the plate 10 prior to downwardly securing the compression ball 30a thereon. In operation, as the compression ball 30a travels down the top threaded section 251a of the bone screw 20a, this pulls the bone screw 20a upwards, such that a top of a post section 27a contacts an underside of the plate 10. As shown in FIG. 2A, the post 27a of the screw 20a comprises a widest section of the screw, and is configured to abut against an extension portion 12 formed on the plate 10. As the compression ball 30a is downwardly threaded on the screw 20a, the bottom of the compression ball 30a compresses inwardly (e.g., via one or more cut-outs 37) into a compression fit with the plate 10, thereby locking the polyaxial motion of the screw 20a relative to the plate 10.

With respect to the second bone screw 20b, which is in a variable position along the length of the plate 10, the bone screw 20b can be polyaxially adjustable relative to plate 10 prior to downwardly securing the compression ball 30a thereon. In addition, the position of the bone screw 20b relative to bone screw 20a can be modified, as the carriage 40 is moved along the length of the track. In operation, as the compression ball 30b travels down the top threaded section 251b of the bone screw 20b, this pulls the bone screw 20b upwards, such that a top of a post section 27b contacts an underside of the plate 10. As shown in FIG. 2A, the post 27b of the screw 20b comprises a widest section of the screw, and is configured to abut against the bottom of the carriage 40. As the compression ball 30b is downwardly threaded on the screw 20b, the bottom of the compression ball 30b compresses inwardly (e.g., via one or more cut-outs 37) into a compression fit with the carriage 40 and plate 10. As the compression ball 30b is downwardly threaded, the post 27b of the screw is pulled upwards to abut and push against the bottom flange 46 of the carriage 40, while the top of the compression ball 30b pulls down on the top flange 42 of the carriage 40, thereby compressing the carriage 40 against the plate 10. Thus, the downward threading of the compression ball 30b on the screw 20b advantageously locks the polyaxial motion of the screw 20b relative to the plate 10, and compresses the carriage 40 to secure the relative position of the screw 20b relative to screw 20a.

Figure 3:
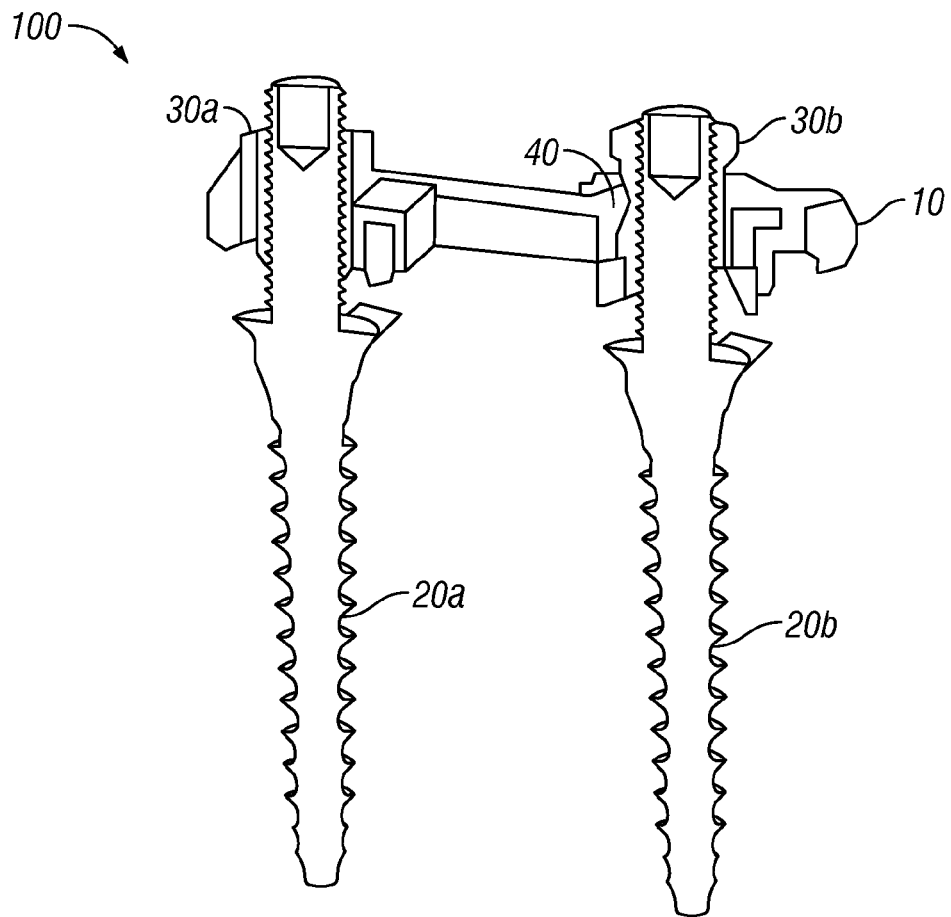
FIG. 3 shows a side cut view of the bone fixation plating device of FIG. 2A.
Figure 4:
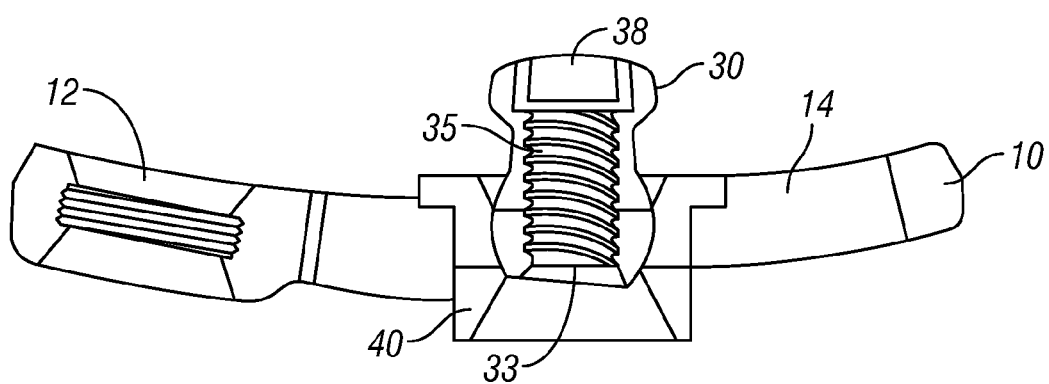
FIG. 4 shows a side cut view of a portion of the bone fixation plating device of FIG. 2A.

FIGS. 3 and 4 show side cut views of the bone fixation plating device 100. In particular, FIG. 3 shows a side cut view of the bone fixation plating device 100 cut along the longitudinal axis of the bone fixation plate 10 and along an axis perpendicular to the longitudinal axes of the posted bone screws 20; and, FIG. 4 shows a side cut view of the bone fixation plate 10 and a locking ball 30 cut along the longitudinal axis of the bone fixation plate 10. As seen in FIG. 4, the locking ball 30, which is an example of a locking device that can be used in the bone fixation plating device 100, comprises an aperture (or opening) 33 and an internal threading 35 that is constructed to receive a portion of the screw 20 and mate with and securely fasten to a corresponding top threaded section 251 (shown in FIG. 7A) of the screw 20. The locking ball 30 can include one or more cut-outs 37 (e.g., shown in FIG. 2A) that are configured to allow a portion of the body of the locking ball 30 to be compressed inward (e.g., in the direction of the aperture 33), so as to firmly secure and lock the locking ball 30 to a portion of screw 20. The locking ball 30 can further include a ratcheting recess 38, which can be configured to receive, e.g., a hexagonal tool such as a hex drive, wrench, or other known tool to rotate the locking ball 30, securing it to the screw 20. The locking ball 30 can include, e.g., a pear-shape, a spherical shape, or any other shape that allows the locking ball 30 and screw 20 to pivot and/or rotate with respect to the bone fixation plate 10.

Figure 5:
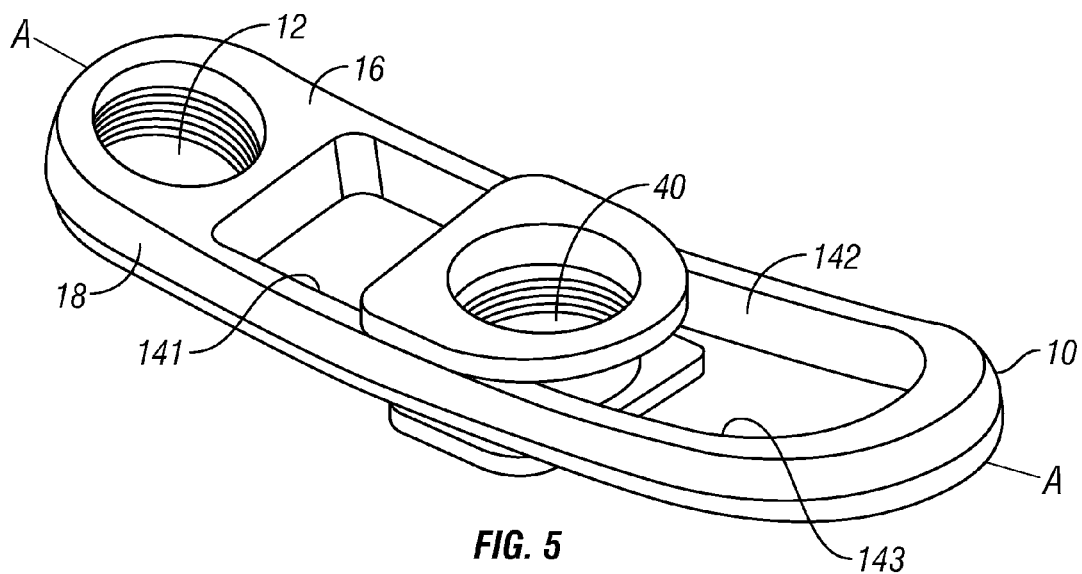
FIG. 5 shows an example of a single-level bone fixation plate that can be include in the bone fixation plating device of FIGS. 1A and 1B.

FIG. 5 shows an example of the bone fixation plate 10 and the carriage 40 that can be included in the bone fixation plating device 100. As shown from this view, the carriage 40 comprises a monolithic member assembled to the plate 10. In other embodiments, the carriage 40 can be formed of two or more members that are rotatably coupled, press-fitted or otherwise secured to one another along the plate 10. As shown in FIG. 5, the carriage 40 occupies only a certain amount of space within the plate 10. Areas adjacent to the carriage 40 can be used to insert other devices, such as spacers, through the plate 10 and into a desired anatomical location. Accordingly, in some embodiments, the fixation plating device 100 can be used with other devices (e.g., spacers) as part of a broader surgical system (e.g., for fusion).

Figure 6:
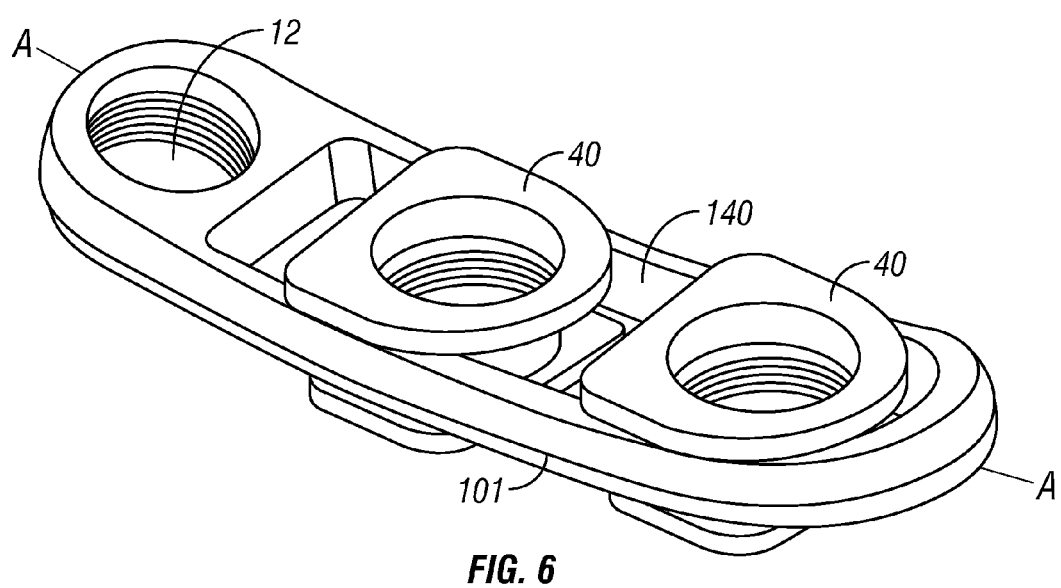
FIG. 6 shows an example of a multi-level bone fixation plate that can be included in the bone fixation plating device of FIGS. 1A and 1B.

FIG. 6 shows an example of a bone fixation plate 101 and a plurality (e.g., two) carriages 40 that can be included in the bone fixation plating device 100. In this embodiment, three screws—one in a relatively fixed position, and two in variable positions along the length of the plate—can be accommodated. The bone fixation plate 101 can be substantially the same as, or similar to the bone fixation plate 10, except that the slot 14 can be lengthened in a longitudinal axis A-A direction of the bone fixation plate to accommodate a plurality of carriages 40.

Referring to FIG. 5, the bone fixation plate 10 can include, e.g., a single-level pre-lordosed plate that can be provided with an integrated carriage 40. The bone fixation plate 10 can include a locking device receiving hole 12 and a carriage receiving slot 14, in which a portion of a screw 20 (e.g., shown in FIG. 1A) can pass through and be used to fasten the bone fixation plate 10 to, e.g., the vertebrae of a spine. The carriage receiving slot 14 can include an inner perimeter that forms a pair of carriage guides 141, 142, and a carriage stop 143. The pair of carriage guides 141, 142 can be substantially parallel to each other along the longitudinal axis A-A. The carriage guides 141, 142 serve to guide and support the carriage(s) 40, allowing the carriage 40 to be moved along the longitudinal axis A-A of the bone fixation plate 10. The carriage stop 143 can function to prevent the carriage 40 from, e.g., falling from the bone fixation plate 10. The bone fixation plate 10 can be secured to, e.g., two vertebrae in order to maintain the vertebrae integrally with respect to one another in a desired orientation and at a desired spacing from one another. The locking device receiving hole 12 and the carriage receiving slot 14 are adjacent to one another along the longitudinal axis A-A of the bone fixation plate 10. The bone fixation plate 10 can be planar and can have length and width dimensions that significantly exceed its thickness dimensions. The bone fixation plate 10, however, can have shapes other than planar, without departing from the scope or spirit of the invention.

The bone fixation plate 10 has an anterior surface 16 and a posterior surface 18. The length of the bone fixation plate 10 along the longitudinal axis A-A is generally greater than its width along its transverse axis B-B. Furthermore, the bone fixation plate 10 can be curved in a longitudinal plane that is parallel to the anterior surface 16 and that includes the longitudinal axis A-A. The bone fixation plate 10 can be curved in a transverse plane that is perpendicular to the anterior surface 16 and that includes the transverse axis B-B. The bone fixation plate 10 can be pre-lordosed or can be curved during surgical implantation.

The direction of the curvature in both the longitudinal and transverse planes can be substantially the same (or different), such that the posterior surface 18 of the bone fixation plate 10 can be concave and the anterior surface 16 can be convex. The radius of the curvature in the longitudinal plane A-A can be selected to match the desired lordosis of the section of the vertebral column to which the bone fixation plate 10 can be affixed. In addition, the radius of curvature in the transverse plane can be selected to conform to the transverse curvature of the anterior surfaces of the vertebrae. The radius of the curvature in the longitudinal plane A-A can, therefore, be different from the radius of curvature in the transverse plane and the curvatures do not necessarily form simple arc shapes.

While the bone fixation plate 1Q can have a generally rectangular shape with rounded corners and edges, other shapes can be utilized. The bone fixation plate 10 can be made of, or include any material, such as, e.g., a metal, an alloy, a synthetic material (e.g., carbon fiber), or any combination thereof, that would allow the plate 10 to maintain its structural integrity while allowing for a desired amount of resiliency. The material used can be, or can include a bio-compatible material. The material is capable of withstanding the conditions of a body over a desired period of time. The bone fixation plate 10 can be formed from a material that minimizes interference with magnetic resonance imaging techniques for post-operative evaluations. The bone fixation plate 10 can be made from, e.g., titanium, cobalt chrome, stainless steel or other alloys or materials that are suitable for surgical implantation.

The locking device receiving hole 12 extends through the entire thickness of plate 10 and is sized to receive a locking device (e.g., the locking ball 30 shown in FIG. 4, or the locking device shown in FIG. 9) that is capable of retaining the bone screw (e.g., shown in FIGS. 7A-7B) in the bony structure (e.g., vertebrae) (not shown) in which it is inserted and prevent the screw from backing out of bone fixation plate 10 after the bone fixation plating device 100 is implanted in a patient. In some embodiments, the portion of plate 10 that defines the locking device receiving hole 12 can comprise ribbing configured to mate with, e.g., cutouts provided in the locking device (shown in FIG. 8C).

The bone fixation plate 10 includes the carriage receiving slot 14 which accommodates a carriage 40 (e.g., shown in FIG. 5 or FIGS. 8A-8C). The carriage receiving slot 14 includes the carriage guides 141, 142, and carriage stop 143, and extends through the entire thickness of plate 10 and has a length (along the longitudinal axis A-A) that is sized to be larger than a carriage 40. Typically, the length of the carriage receiving slot 14 is large enough to integrate at least one carriage 40 with space remaining on one or both sides of the carriage 40. The space remaining on either or both sides of the carriage 40 can advantageously provide one or more windows in the plate 10 through which a surgeon can access the bony anatomy beneath the posterior lumbar implant device 100. In some embodiments, additional devices, such as spacers, can be inserted through these windows, such that the plate device 10 and spacers can be part of a broader fusion system. The width of the carriage receiving slot 14 (i.e., the distance between the guides 141, 142, along the transverse axis B-B) is sized to engage an outside surface of an intermediate portion of a carriage so that the carriage 40 is securely retained in the carriage receiving slot 14.

FIG. 6 shows another example of a bone fixation plate 101 that can be included in the bone fixation plating device 100 (e.g., shown in FIG. 1A). The bone fixation plate 101 includes a multi-level plate. In the bone fixation plate 101, the length of a carriage receiving slot 140 (along the longitudinal axis A-A) is sized to be larger than two or more carriages 40 such that two or more carriages can be integrated into plate 10. The length of the carriage receiving slot 140 is large enough to integrate at least two carriages 40 with space remaining between each of the two carriage assemblies and/or space remaining on one side of at least one of the two carriages. The space remaining between each of the two carriages and/or space remaining on one side of at least one of the two carriages provides one or more windows in the plate 101 through which a surgeon can access the bony anatomy beneath the posterior lumbar implant.

Figure 7A:
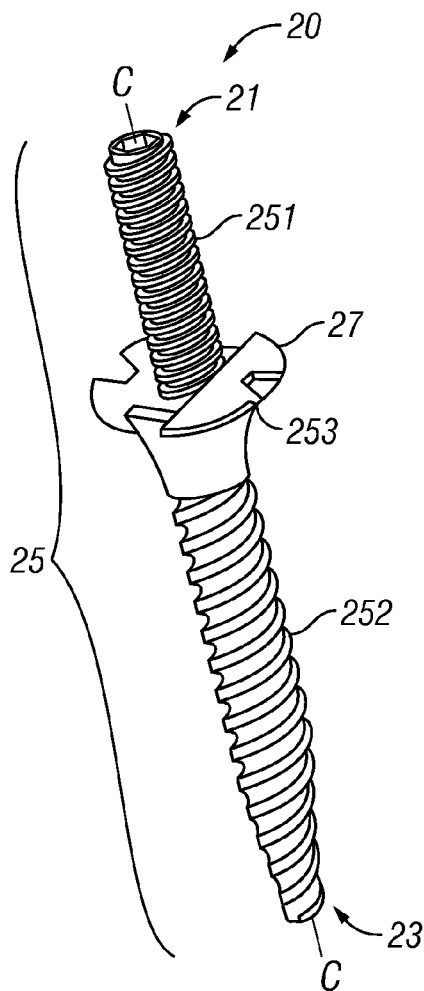
FIGS. 7A and 7B depict examples of the bone screw that can be used in a bone fixation plating device.

FIG. 7A shows an enlarged view of the bone screw 20, which can be included in the bone fixation plating device 100 (e.g., shown in FIG. 1A). The bone screw 20 comprises a proximal end 21, a distal end 23 and a threaded shaft 25 extending distally from the proximal end 21 along a longitudinal axis C-C. The threaded shaft 25 can include two more different types of threading, including, first threading of a top threaded section 251 and a second threading of a bottom threaded section 252. In some embodiments, the first threading of the top threaded section 251 can be a fine threading that is configured to engage and securely fasten to the screw 20 to a locking device (e.g., the locking ball 30 shown in FIG. 1A). The second threading of the bottom threaded section 252 can be a coarse threading that is configured to engage and securely fasten the screw 20 to, e.g., a bone. In some embodiments, the pitch of the threads of the top threaded section 251 differs from the pitch of the threads of the bottom threaded section 252. The top threaded section 251 and bottom threaded section 251, 252 can have different or substantially the same diameters. The first and/or second threads of the different threaded sections 251, 252 can have varying diameters.

In some embodiments, the proximal end 21 of the bone screw 20 can be shaped to mate with a tool adapted to rotate the screw 20 (e.g., to rotate the screw 20 in order to implant the screw into a bony structure). For instance, the proximal end 21 of the bone screw 20 can comprise a hexagonal recess that receives a hexagonal tool such as a hex drive, or a slot or cross that receives a screwdriver. The bone screw 20 can further comprise a post 27 that is positioned between the distal end 23 and the proximal end 21. The post 27 extends away from the threaded shaft 25 in a plane that is substantially perpendicular to the longitudinal axis C-C.

The bone screw 20 is comprised of, e.g., a metal, an alloy, a synthetic material, or any combination thereof. The bone screw 20 is typically made of a material that allows the screw to maintain its structural integrity while allowing for a desired amount of resiliency. The material used is usually bio-compatible and is capable of withstanding the conditions of a body over a desired period of time.

As seen in FIG. 7A, the threaded shaft 25 of the bone screw 20 can be tapered at the distal end 23 and an outer perimeter of the post 27 can comprise notches 253 that can be engaged by a tool (not shown) to rotate and drive the screw 20 into bony tissue (not shown).

Figure 7B:
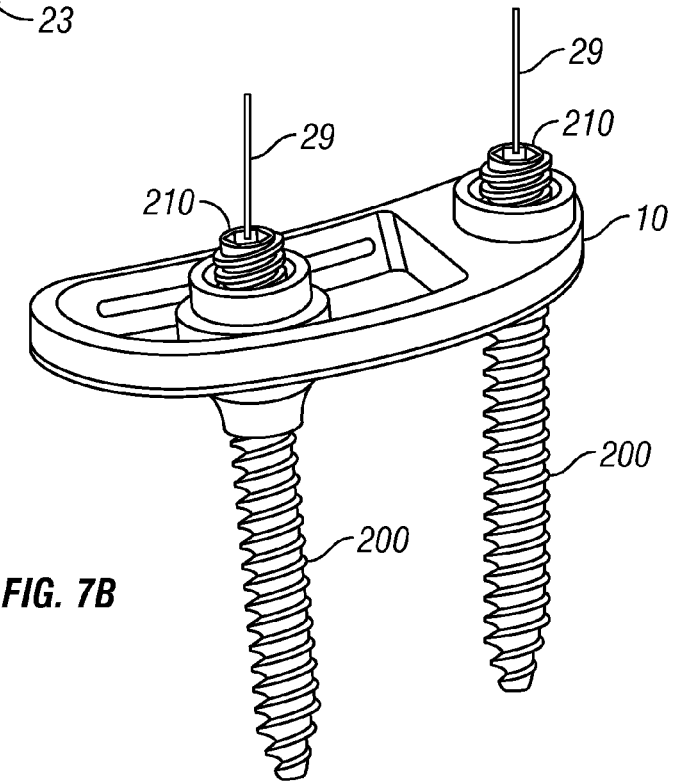

FIG. 7B shows another example of a bone screw 200 that can be included in the bone fixation plating device. The proximal end 210 of the screw 200 can comprise an open-ended guide wire capture slot to accommodate a guide wire 29. Utilization of a guide wire 29 in each of the bone screws 200 can enable a surgeon to position the locking device receiving hole 12 and carriage 40 of a plate 10 over the bone screws 200 more easily than in cases where the guide wire 29 is not employed.

Figure 8A:
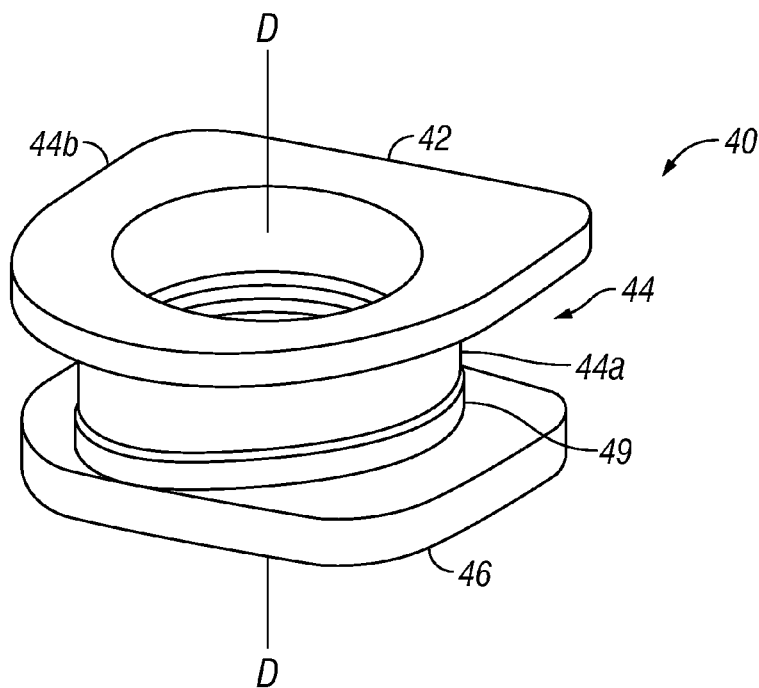
FIGS. 8A and 8B depict examples of a carriage that can be included in the bone fixation plating device of FIG. 1A.

FIG. 8A shows an example of the carriage 40 that can be included in the bone fixation plating device. In some embodiments, the carriage 40 can be monolithic. In other embodiments, the carriage 40 can be formed of multiple pieces (e.g., rotatably coupled together). The carriage 40 comprises an upper flange 42 and a lower flange 46 connected by (or integrally formed with) an intermediate portion (guide) 44 along an axis D-D. The intermediate portion 44 comprises an outside surface 44a and an inside surface 44b. The inside surface 44b defines a locking device receiving hole and the outside surface 44a is configured to mate with the carriage guides 141, 142 in the plate 10 (e.g., shown in FIG. 5). In some embodiments, the inside surface 44b can comprise ribbing configured to engage with the outside surface of the intermediate portion of the locking device (e.g., locking ball 30 shown in FIG. 1A) to securely hold the locking device in the locking device receiving hole once the locking device is inserted therein. The inside surface 44b can include, e.g., a flared surface portion that is constructed to allow the locking device to pivot and/or rotate about the axis D-D. Advantageously, the carriage 40 is provided with a series of surface cuts 49, which increase the compressibility of the carriage 40.

The carriage 40 can be made of the same material as (or a different material from) the plate 10. The carriage 40 can be made of a material that comprises, e.g., a metal, an alloy, a synthetic material, or any combination thereof. The material can be bio-compatible and capable of withstanding the conditions of a body over a desired period of time. Carriage 40 can be formed from a material that minimizes interference with magnetic resonance imaging techniques for post-operative evaluations. The carriage 40 can be made of a material that comprises, e.g., titanium, cobalt chrome, stainless steel or other alloys or materials that are suitable for surgical implantation.

Figure 8B:
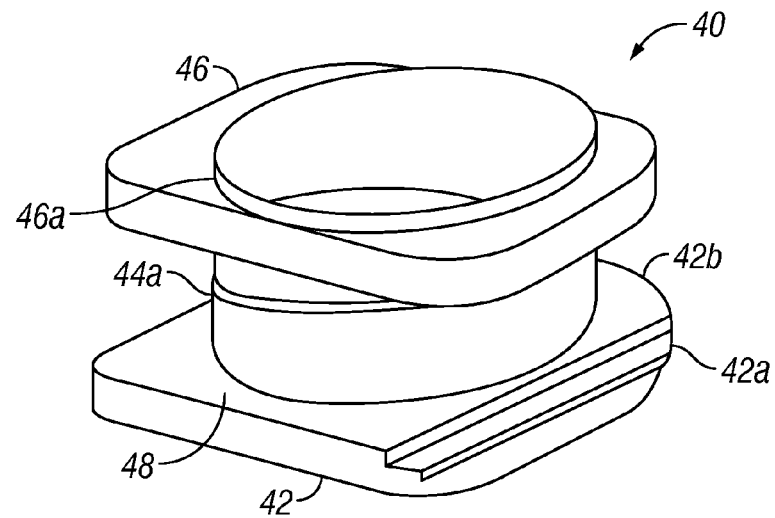

FIG. 8B shows the undersides of the upper flange 42 and lower flange 46 of the carriage 40 of FIG. 8A in further detail. In particular, the underside of the upper flange 42 can comprise an indentation 42a along one (or two) of the edges of the flange 42 that reduces the thickness of the upper flange 42 so that it can contact and engage the anterior surface 16 of the plate 10 (e.g., the guide 141, 142 shown in FIG. 5). More specifically, the indentation 42a allows the upper flange 42 to engage and overlap with the anterior surface 16 of the portion of the plate 10 that defines the guides 141, 142 of the carriage receiving slot 14, thereby preventing the upper flange 42 from twisting or turning while securely, with the assistance of the lower flange 46, holding the carriage 40 in the plate 10. The lower flange 46 can also include a similar indentation (not shown) to the indentation 42a.

Also seen in FIG. 8B is the underside of the lower flange 46 of the carriage assembly 40 shown in FIG. 8A. As seen in FIG. 8B, the underside of the lower flange 46 of the carriage 40 can comprise a reverse bevel 46a. When the proximal end 21 of the bone screw 20 is inserted into and through the locking device receiving hole of the carriage 40 (or plate 10), and then into the aperture 33 (e.g., shown in FIG. 4) in the locking device, the locking device can be turned to mate the locking device 30 to the screw 20 and pivotally fasten the locking device and screw 20 to the carriage 40 (or plate 10). The reverse bevel 46a can engages with the post 27 in the bone screw 20 to provide a pivot stop for the screw 20 and locking device 30, thereby preventing the screw 20 from pivoting beyond a predetermined threshold (e.g., about 25°) with respect to the normal to the plane of the plate 10.

The locking device receiving hole 12 of plate 10 and the locking device receiving hole of the carriage 40 (e.g., shown in FIG. 4) allow the bone screw 20 to be inserted in through and locked at an angle of (in some embodiments), e.g., between about 0° and 25° away from normal axis to the plane of plate 10 and of the carriage 40 (e.g., at an angle of about 0° and 25° away from an axis that is perpendicular to the plane of plate 10 and at an angle of, e.g., about 0° and 25° away from the axis D-D of the carriage 40, respectively).

FIG. 8B illustrates further details of the outside surface 44a of the intermediate portion 44 of the carriage 40. As seen, the outside surface 44a of the intermediate portion 44 can comprise a helical groove 48 that aids the carriage 40 in translating along the longitudinal axis A-A of the carriage receiving slot 14. The helical groove 48 can enable the carriage 40 to lock into a particular position within the carriage receiving slot 14.

Figure 9:
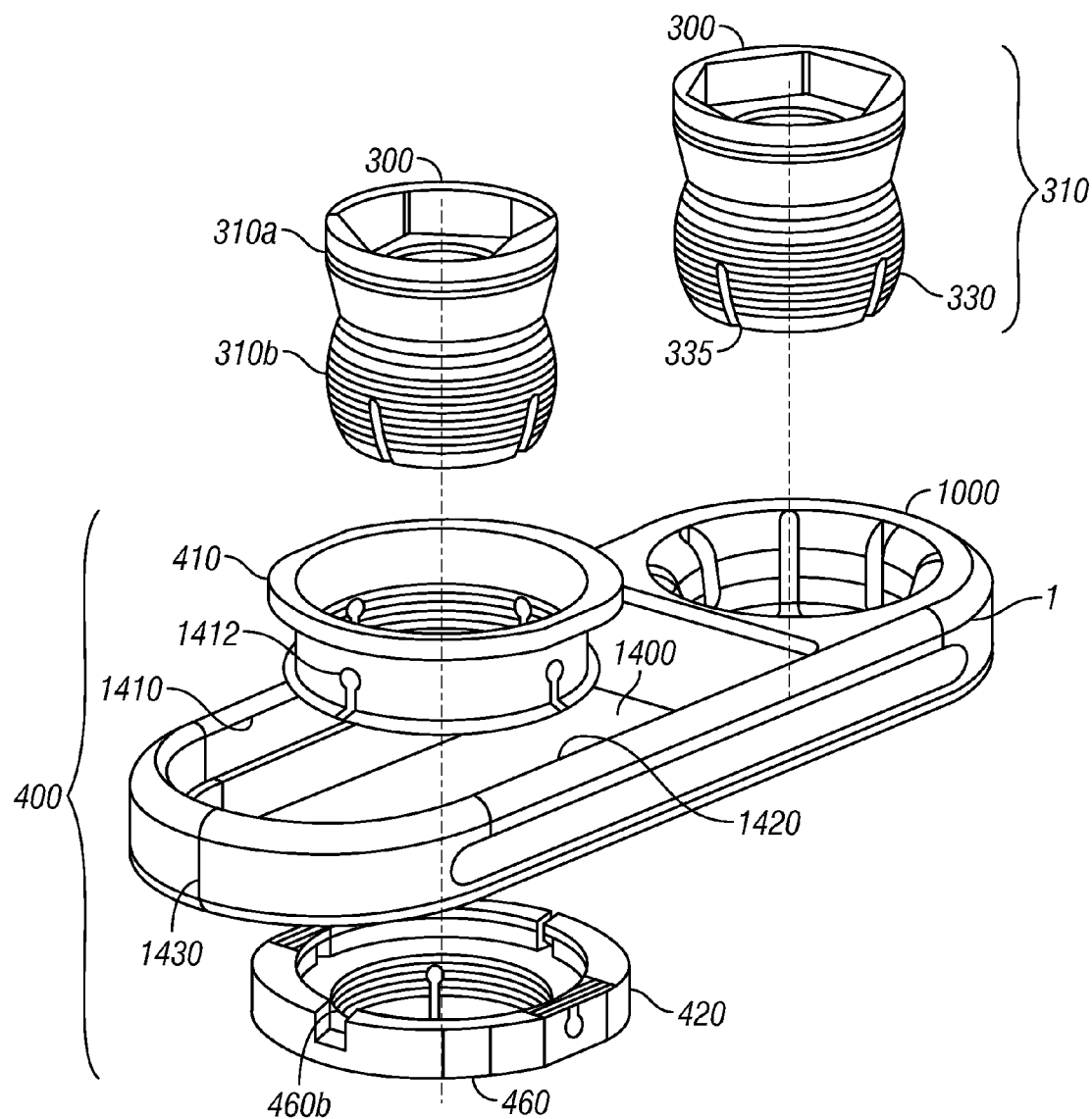
FIG. 9 shows another embodiment of a bone fixation plating device according to some embodiments.

FIG. 9 illustrates another example of a bone fixation plate 1000, a carriage 400, and a plurality of locking devices 300. In some embodiments, the locking devices 300 are of similar construction to the compression balls described above.

The bone fixation plate 1000 includes a carriage receiving slot 1400, which comprises a pair of substantially parallel guides 1410, 1420. The carriage receiving slot 1400 can further include a carriage stop 1430. The walls of the guides 1410, 1420 and the carriage stop 1430 can be, e.g., annular, substantially flat, or have any other surface shape that can engage and secure the carriage 400 to the bone fixation plate 1000.

The carriage 400 comprises an upper carriage portion 410 and a lower carriage portion 420. The upper carriage 410 can include a plurality of cutouts 1412. The bottom carriage 420 can be configured such that it securely mates with the upper carriage 410 via a rotational fit, a press fit, a compression fit or other type of fit. In some embodiments, the cutouts 1412 of the upper carriage portion 410 can allow the lower edge of the upper carriage portion 410 to expand and securely engage the lower carriage portion 420, thereby forming a single-piece carriage that can ride along the rails of the plate 1000.

The carriage 400 can be moved along the longitudinal axis A-A of the carriage receiving slot 1400 of the plate 1000. When the carriage 400 translates along the longitudinal axis A-A of the carriage receiving slot 1400, the relative position of the bone screws 20a and 20b associated with the plate 1000 is changed and dynamic compression (or expansion) is provided between multiple bony structures secured to the plate 1000. The carriage 400 can be configured to allow for polyaxial pivoting and/or rotation of a screw received within the carriage until a locking device 300 is inserted therein and fastened to the carriage 400, As described above, a screw 20b (e.g., a pedicle screw) can extend through the carriage 400 and the plate 1400. The locking device 300 can be downwardly threaded onto the screw 20b, thereby compressing the upper carriage 410 and lower carriage 420 in a like manner as discussed above. Once the locking device 300 is downwardly threaded, this helps lock the polyaxial angle of the screw 20b relative to the plate 10, as well as the relative distance between the screw 20b and another screw 20a received within the plate.

The locking device 300 comprises a main body 310 having an upper portion 310a, a lower portion 310b, a top 310c and a bottom 310d. The top 310c of the locking device 300 can be shaped to mate with a tool adapted to rotate the locking device 300 (e.g., to rotate the locking device 300 within the locking device receiving hole of the carriage 400, or plate 1000, such that the locking device 300 mates with the carriage 400 or plate 1000). For instance, the top 310c of the locking device 300 can comprise a hexagonal recess (as shown in FIG. 8C) that receives a hexagonal tool such as a hex drive, or a slot or cross that receives a screwdriver. Alternatively, the top 310c of the locking device 300 can be configured with a protruding engagement surface that can engage with a tool or device having a corresponding recess. The upper portion 310a, together with the top 310c, defines an aperture dimensioned to receive a bone screw 20 that transcends through the lower portion 310b of the locking device.

The lower portion 310b of the locking device 300 comprises an outside surface 330 and an inside surface (not shown). The outside surface 330 is shaped and configured to mate with the locking device receiving hole of the carriage 400 and/or the plate 1000. The lower portion 310b can comprise cutouts 335 that are capable of compression to enable lockable mating with ribbing in the locking device receiving hole of carriage assembly 400 and/or plate 1000. The locking device 300 comprises an aperture (not shown) that is dimensioned to receive a bone screw 20. The inside surface (not shown) of locking device 300 can comprise threading that is capable of mating with the threads of the threaded shaft 25 of a bone screw 20.

In some embodiments, the aperture (not shown) in the locking device 300 can be a keyhole-shaped passage (not shown) that includes a central cylindrical portion (not shown) that receives the proximal end 21 of a bone screw 20. The cutouts 335 permit expansion and reduction in the size of the central cylindrical portion. When the size of the central cylindrical portion is reduced, the proximal end 21 of the bone screw 20 is secured within the locking device 300.

The outside surface of the upper portion 310a can have a shape of, e.g., a bowl, a cup, a cone, or the like, wherein a top part of the upper portion 310a can have a diameter that is the same or different from the diameter of the bottom part of the upper portion 310a. The outside surface 330 of the lower portion 310b of the locking device 300 can have an inverted shape to that of the upper portion 310a, such that the upper portion 310a and lower portion 310b can be mirror images of one another when viewed relative to a longitudinal axis E-E. Alternatively, the upper portion 310a and lower portion 310b can be shaped differently.

Figure 10:
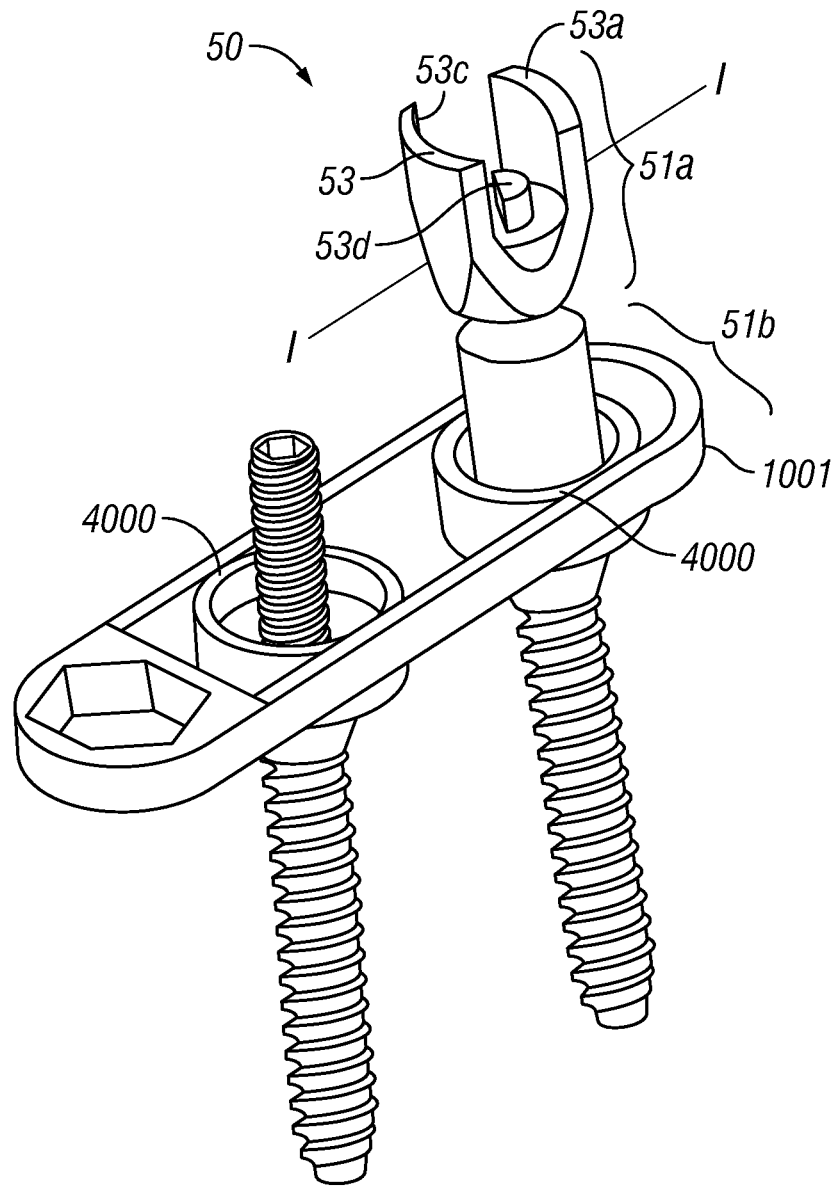
FIG. 10 shows another embodiment of a bone fixation plating device according to some embodiments.

FIG. 10 shows an example of a bone fixation plating device 1001 that comprises a locking device 50 including a tulip shaped attachment. Advantageously, the tulip shaped attachment can receive other implants (e.g., rods) to assist in future revisions to the system. In some embodiments, the tulip shaped attachment is detachable from the rest of the locking device.

The locking device 50 comprises a main body 51 having an upper portion 51a and a lower portion 51b. The upper portion 51a of the locking device 50 is defined by an outside wall 53 which has a proximal end 53a and a distal end 53b. The outside wall 53 can comprise two open-ended slots 53c and 53d positioned opposite of one another relative to a longitudinal axis I-I. The two open-ended slots 53c and 53d can extend distally from the proximal end 53a to the distal end 53b of the outside wall 53 and can be sized to receive a rod.

The distal end 53b of the outside wall 53 can comprise a screw-receiving aperture (not shown) that transcends the distal end 53b of the upper portion 51a to reach the lower portion 51b. The screw-receiving aperture (not shown) can be large enough to receive the proximal end 21 of a bone screw 20 inserted through the lower portion 51b of the locking device 50, or another fastening device to be used with a rod.

The lower portion 51b can be shaped e.g., as an inverted bowl or cup, wherein the upper part of the lower portion 51b can have a diameter that is smaller than the diameter of the lower part of the lower portion. The lower portion 51b of the locking device comprises an outside surface 55 and an inside surface (not shown). The outside surface 55 can be shaped and configured to mate with the locking device receiving hole of the carriage 40 and/or of plate 10. Typically, the outside surface 55 comprises threads that are capable of threadably mating with ribbing in the locking device receiving hole of a carriage 4000 and/or a plate 1010.

The inside surface (not shown) defines an aperture (not shown) that is dimensioned to receive a bone screw 20 according to the disclosure. The aperture (not shown) can be a keyhole-shaped passage (not shown) that includes a central cylindrical portion (not shown) that receives a bone screw 20 and one or more cutouts (not shown) which permit expansion and reduction in the size of the central cylindrical portion. When the size of the central cylindrical portion is reduced, the bone screw 20 is secured within the tulip-shaped locking device 50.

Referring to FIG. 1A, the bone fixation plate device 100 can be delivered to, and implanted into a patient. A method of implanting the bone fixation plate device 100 can include drilling one or more holes into a location of one or more bony structures (e.g., vertebrae) in the patient. A first screw 20a and plate 10 having a carriage 40 attached thereon can be provided, wherein the first screw 20a is polyaxially adjustable relative to the plate 10. The first screw 20a extends through a first slot in the plate 10 and can be inserted into the hole in the vertebrae. A compression ball 30a can be downwardly threaded onto the top of the first screw 20a to thereby secure the angle of the screw 20a relative to the plate 10. A second screw 20b can also be provided and inserted into a hole formed in the vertebrae. The second screw 20b can extend through the carriage 40 of the plate 10, which can slide along a length of the plate 10. Like the first screw 20a, the second screw 20b is polyaxially adjustable relative to the plate 10. A compression ball 30b can be downwardly threaded on to the top of the second screw 20b to thereby secure the angle of the screw 20b relative to the plate 10. The compression ball 30b also helps to compress the carriage 40, thereby securing the relative position of the second screw 20b relative to the first screw 20a.

In other embodiments, both screws 20a and 20b are inserted into predetermined holes formed in the vertebrae.

Once the screws 20 are properly secured and in position, a bone fixation plate 10 having an appropriate length and curvature can be selected. In some embodiments, the bone fixation plate 10 can be preselected based on the desired spacing between the screws 20, so as to provide the proper spacing between the screw receiving opening 12 in the plate 10 and the screw receiving opening in the carriage 40. The plate 10 can be pre-curved for both lordotic and extra-lordotic conditions. Additional contouring can be possible utilizing an instrument (not shown) to bend or twist the plate 10 based on anatomical needs of the particular patient.

Once the plurality of bone screws 20 are securely and properly affixed to (or in) the one or more bony structures, and the proper bone fixation plate 10 has been selected (and/or reconfigured to meet anatomical needs), the bone fixation plate 10 can be positioned near and the openings in the plate 10. One opening of the plate 10 can align with the first screw 20*a*, while a second opening of the plate 10 including a carriage 40 can be aligned with the proximal end 21 of a second screws 20*b*. The carriage 40 in the bone fixation plate 10 can be moved in the bone fixation plate 10 along the longitudinal axis of the bone fixation plate 10 to provide appropriate spacing, if necessary. After proper alignment of the bone fixation plate 10 to the bone screws 20*a* and 20*b*, the bone fixation plate 10 (including the carriage 40) can be moved toward and mounted on the bone screws 20, such that the locking device receiving hole 12 of the posterior surface 18 of bone positioning plate 10 mounts over and on to the proximal end 21 of the first bone screw 20*a* and the locking device receiving hole of the carriage 40 mounts over and on to the proximal end 21 of the second bone screw 20*b*. As noted earlier, guide wires 29 can be provided (e.g., shown in FIG. 7B) to facilitate easier alignment of the screws 20 to the openings in the plate 10 and carriage 40.

After the bone fixation plate 10 is mounted on the first and second bone screws 20, one or more locking devices 30 can be threaded onto the proximal end 21 of the first bone screw 20*a* and then onto the proximal end 21 of the second bone screw 20*b*. This can be accomplished by taking a first locking device 30*a* and fastening it to the first bone screw 20*a*, and then reducing it into the plate 10 (or carriage 40) by turning the locking device 30*a* until it securely engages and locks to the plate 10 (or carriage 40). Similarly, a second locking device 30*b* can be fastened to the remaining screw 20*b* and then reduced into the carriage 40 (or plate 10) until it securely engages and locks to the carriage 40 (or plate 10). In some embodiments, the spacing between the carriage 40 and opening 12 in the plate 10 can be adjusted after one of the screws 20 has been secured and locked to the carriage 40 (or plate 10), but before the remaining screw 20 has been locked to the plate 10 (or carriage 40).

The first and second bone screws 20 can be screwed into one or more bony structures at an angle that is (in some embodiments), e.g., between about 0° and 25° away from the axis normal to the plane of the plate 10. Because the screws 20 are not constrained to being inserted at an angle that is perfectly perpendicular to the longitudinal axis A-A of the plate 10, the screws 20 can be closely spaced without interfering with one another. In some embodiments, the first and second bone screws 20 can be inserted into, e.g., adjacent vertebrae.

As noted earlier, the proximal end 21 of the first and second bone screws 20 can comprise an open-ended guide wire capture slot to accommodate the guide wire 29. Guide wires 29 can be inserted into the open-ended guide wire capture slots of the screws 20 after the distal end 23 of each of the screws 20 are screwed into the one or more bony structures.

One or more than one carriage 40 can be mated with the carriage receiving slot 14 of the plate 10. When only one carriage 40 is mated with the carriage receiving slot 14 of the plate 10, the plate 10 is a single-level plate. When more than one carriage 40 is mated with the carriage receiving slot 14 of the plate 10, the plate 10 is a multi-level plate.

While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications or modifications of the invention.

What is claimed is:

1. A bone fixation plating device for therapeutic treatment of a patient, the device comprising:
    a plate having a locking device receiving hole and a carriage receiving slot, wherein the locking device receiving hole and the carriage receiving slot are adjacent to one another and the locking device receiving hole is configured to receive and pass there-through a portion of a first screw, wherein the carriage receiving slot includes at least one guide; and
    a carriage comprising an intermediate portion that is configured to fit in the carriage receiving slot, the carriage comprising a hole to receive and pass there-through a portion of a second screw, wherein the carriage comprises an upper flange and a lower flange, wherein the upper flange is capable of moving downward toward an upper surface of the at least one guide and the lower flange is capable of moving upward toward a lower surface of the at least one guide;
    a first locking device having a first compression ball coupled to the first screw and a second locking device having a second compression ball coupled to the second screw, the first and second compression balls configured to pivot and/or rotate with respect to the plate,
    wherein the second compression ball engages a portion of the upper flange of the carriage, and
    wherein the upper flange is rotatably coupled to the lower flange.

2. The device of claim 1, wherein at least one of the upper flange and the lower flange comprises an indentation that is configured to engage the at least one guide.

3. The device of claim 1, wherein at least one of the upper flange and the lower flange comprises a reverse bevel.

4. The device of claim 1, further comprising:
    a further carriage that is configured to fit in the carriage receiving slot together with said carriage, said further carriage comprising a hole to receive and pass there-through a portion of a screw, wherein said carriage and said further carriage are movable in the carriage receiving slot along a longitudinal axis of the plate.

5. The device of claim 1, wherein the first screw comprises a post.

6. The device of claim 5, wherein the first screw further comprises: a first thread and a second thread, wherein one of the first and second threads comprises a fine thread.

7. The device of claim 6, wherein the other of the first and second threads of the first screw comprises a coarse thread.

8. The bone fixation plating device of claim 1, wherein each of the two bone screws comprises a threaded shaft that is tapered at the distal end.

9. A bone fixation plating device for therapeutic treatment of a patient, the device comprising:
- a plate having a locking device receiving hole and a carriage receiving slot, wherein the locking device receiving hole and the carriage receiving slot are adjacent to one another and the locking device receiving hole is configured to receive and pass there-through a portion of a first screw, wherein the carriage receiving slot includes at least one guide;
- a carriage comprising an intermediate portion that is configured to fit in the carriage receiving slot, the carriage comprising a hole to receive and pass therethrough a portion of a second screw, wherein the carriage comprises an upper flange and a lower flange, wherein the upper flange is capable of moving downward toward an upper surface of the at least one guide and the lower flange is capable of moving upward toward a lower surface of the at least one guide; and
- a plurality of locking devices that are configured to fasten to said first and second screws and secure the plate to the first and second screws,
- wherein the locking devices includes a first compression ball coupled to the first screw and a second compression ball coupled to the second screw, the first and second compression balls configured to pivot and/or rotate with respect to the plate,
- wherein the second compression ball engages a portion of the upper flange of the carriage, and
- wherein the upper flange is rotatably coupled to the lower flange.

10. The device of claim 9, wherein the carriage is movable in the carriage receiving slot along a longitudinal axis of the plate.

11. The device of claim 9, wherein at least one of the upper flange and the lower flange comprises an indentation that is configured to engage the at least one guide.

* * * * *